(12) United States Patent
Schreiner et al.

(10) Patent No.: US 6,380,183 B1
(45) Date of Patent: Apr. 30, 2002

(54) TREATMENT OF DISEASES INVOLVING CYST FORMATION

(75) Inventors: George F. Schreiner, Los Altos Hills; Alison Joly, San Mateo; Lawrence W. Stanton, Redwood City; R. Tyler White, Fremont, all of CA (US)

(73) Assignee: Scios, Inc., Sunnyvale, CA (US)

( * ) Notice: Subject to any disclaimer, the term of this patent is extended or adjusted under 35 U.S.C. 154(b) by 0 days.

(21) Appl. No.: 09/461,910

(22) Filed: Dec. 15, 1999

Related U.S. Application Data

(60) Provisional application No. 60/113,008, filed on Dec. 18, 1998, now abandoned, and provisional application No. 60/136,208, filed on May 26, 1999.

(51) Int. Cl.$^7$ .............................................. A61K 31/55

(52) U.S. Cl. .................................................. 514/211.06
(58) Field of Search ..................................... 514/211.06

(56) References Cited

U.S. PATENT DOCUMENTS

| | | | |
|---|---|---|---|
| 4,808,599 A | 2/1989 | Dubroeucq et al. ......... | 514/320 |
| 5,026,711 A | 6/1991 | Mendes et al. ............. | 514/300 |
| 5,128,338 A | 7/1992 | Bourguignon et al. ... | 514/233.2 |
| 5,776,946 A | 7/1998 | McGeer et al. ............. | 514/307 |
| 5,882,881 A | 3/1999 | Woo ........................... | 435/30 |

FOREIGN PATENT DOCUMENTS

| | | |
|---|---|---|
| WO | WO94/08041 | 4/1994 |
| WO | WO 94/08041 | 4/1994 |
| WO | WO 96/32383 | 10/1996 |

OTHER PUBLICATIONS

Reeders et al., A highly polymorphic DNA marker linked to adult polycystic kidney disease on chromosome 16, *Nature* 317:542–544 (1985).

Kimberling et al., "Autosomal dominant polycystic kidney disease: localization of the second gene to chromosome 4q13–q23," *Genomics* 18:467–472 (1993).

Daoust et al., "Evidence for a third geentic locus for autosomal dominant polycystic kidney disease," *Genomics* 25:733–736 (1995).

Koptides et al., "Germinal and somatic mutations in the PKD2 gene of renal cysts in autosomal dominant polycystic kidney diseases,"*Hum. Mol. Genet.* 8:509–513 (1999).

Preminger et al., "Murine congenital polycystic kidney disease: a model for studying development of cystic disease," *J. Urol.* 127:556–560, 1993.

Davisson et al., "The mouse Polycystic Kindey Disease Mutation (cpk) is Located on Proximal Chromosome 12,"*Genomics* 9:778–781 (1991).

Mücher et al., "Fine mapping of the autosomal recessive polycystic kidney disease locus (PKHD1) and the genes MUT, RDS, CSNK2α, and GSTA1 at 6p21.1–p12," *Genomics* 48:40–45 (1998).

Woo et al., "Taxol inhibits progression of congenital polycystic kidney disease," *Nature* 368:750–753 (1994).

J. Grantham, "The eitology, pathogenesis, and treatment of autosomal dominant polycystic kidney disease: recent advances," *Am. J. Kid. Dis.* 28:788–803 (1996).

Adinoff et al., "Vagal tone decreases following diazepam," *Psychiatry Research* 41:89–97 (1992).

DiMicco, "Evidence for control of cardiac vagal tone by benzodiazepine receptors," *Neuropharmacology* 26:553–559 (1987).

Edoute et al., "Ro 5–4864 and PK 11195, but not diazepam, depress cardiac function in an isolated working rat heart model," *Pharmacology* 46:224–230 (1993).

Grupp et al., "Benzodiazepine Ro 5–4864 increases coronary flow," *Eur. J. Pharm.* 143:143–147 (1987).

Leeuwin et al., "PK 11195 antagonizes the positive inotropic of the isolated rat heart to diazepam but not the negative inotropic response," *Eur. J. Pharm.* 299:149–152 (1996).

Leeuwin et al., "Actions of enzodiazepines on the inotropy of the perfused rat heart,"*Arch. Int. Pharmacodyn.* 326:5–12 (1993).

Shany et al., "Ro 5–4864 has a negative inotropic effect on human atrial muscle strips that is not antagonized by PK 11195," *Eur. J. Pharm.* 253:231–236 (1994).

Mestre et al., "Electrophysiological and pharmacological characterization of peripheral benzodiazepine receptors in a guinea pig heart preparation," *Life Sciences* 35;953–962 (1984).

Charbonneau et al., "Peripheral–type benzodiazepine receptors in the living heart characterized by positron emission tomography," *Circulation* 73:476–483 (1986).

Davies and Huston, "Peripheral benzodiazepine binding sites in heart and their interaction with dipyridamole," *Eur. J. Pharm.* 73:209–211 (1981).

Kruger et al., "Purification, Cloning and Expression in a Peripheral–type Benzodiazepine Receptor," *in: GABA and Benzodiazepine Receptor Subtypes*, Biggio and Costa eds., pp. 1–14 (1990).

Sprengel et al., "Molecular cloning and expression of cDNA encoding a peripheral–type benzodiazepine receptor,"*J. Biol. Chem.* 264:20,415–20, 421 (1989).

(List continued on next page.)

*Primary Examiner*—Dwayne C. Jones
(74) *Attorney, Agent, or Firm*—Knobbe, Martens, Olson & Bear LLP

(57) ABSTRACT

The invention concerns the use of ligands of peripheral-type benzodiazepine receptors (PTBR) in the diagnosis and treatment of diseases involving cyst formation and in particular polycystic kidney disease. The invention further concerns the treatment of hypertension accompanying polycystic kidney disease, and pharmaceutical compositions and articles of manufacture for the treatment or diagnosis of the target disease or condition.

24 Claims, 6 Drawing Sheets

OTHER PUBLICATIONS

Parola et al., "Cloning and expression of a pharmacologically unique bovine peripheral–type benzodiazepine receptor isoquinoline binding protein," *J. Biol. Chem.* 266:14, 082–14, 087 (1991).

Riond et al., "Molecular cloning and chroomosomal localizatin of a human periphreral–type benzodiazepine receptor," *Eur. J. Biochem.* 195:305–311 (1991).

Garnier et al., "In vitro reconstitution of a functional peripheral–type benzodiazepine receptor from mouse leydig tumor cells," *Mol. Pharmac.* 45:201–211 (1993).

Smith et al., "Comparison of biosequences," *Adv. Appl. Math.* 2:482 (1981).

Needleman et al., "A general method applicable to the search for similarities in the amino acid sequence of two proteins," *J. Mol. Biol.* 48:443 (1970).

Pearson et al., "Improved tools for biological sequence comparison," *Proc. Natl. Acad. Sci. USA* 85:2444 (1988).

Altschul et al., "Gapped BLAST and PSI–BLAST: a new generation of protein databases search programs," *Nucleic Acids Res.* 25:3389–3402 (1997).

Berkovich et al., "A natural processing product of rat diazepam binding inhibitor, triakontatetraneuropeptide (diazepam binding inhibitor 17–50) contains an ∀–helix, which allows discrimination between benzodiazepine binding site subtypes," *Mol. Pharmac.* 37:164–172 (1990).

Guidotti., :Diazepam binding inhibitor (DBI): a peptide with multiple biological actions, *Life Sci.* 49(5):325–44 (1991).

Besman et al., "Identification of des–(Gly–Ile)–endozepine as an effector of corticotropin–dependent adrenal steroidogenesis: Stimlation of cholesterol delivery is mediated by the peripheral benzodiazepine receptor," *Proc. Natl. Acad. Sci. USA* 86:4897–4901 (1989).

Taketani et al., "Involvement of peripheral–type benzodiazepine receptors in the intracellular transport of Heme and Porphyrins," *J. Biochem,* 117:875–880 (1995).

Anzini et al., "Molecular basis of peripheral vs central benzodiazepine receptor selectivity in a new class of peripheral benzodiazepine receptor ligands related to alpidem," *J. Med. Chem.* 4275 (1996).

Cappelli et al., "Mapping the peripheral benzodiazepine receptor binding site by conformationally restrained derivatives of 1–(2–Chlorophenyl)–N–methyl–N–(1–methylpropyl)–3–isoquinolinccarboxamide (PK11195)," *J. Med. Chem.* 2910 (1997).

Schoemaker et al., "Specific high–affinity binding sites for [$_3$H]Ro–5 4864 in rat brain and kidney," *J, Pharmacol. Exp. Ther.* 285:61–69 (1983).

Kaspari–Rittinghausen et al., "A new rat model for polycystic kidney disease of humans," *Transplant Proc.* 6:2582–3 (1990).

Cowley et al., "Autosomal–dominant polycystic kidney disease in the rat," *Kidney Int.* 43:522–34 (1993).

Arola et al., "Experimental Myocarditis induced by two–different coxsackievirus B3 variants: aspects of pathogenesis and comparison of diagnostic methods," *J. Med. Virol.* 47:251–259 (1995).

Chow et al., "Differential effects of myocarditic variants of coxsackievirus B3 in inbred mice, A pathologic characterization of heart tissue damage," *Lab. Invest.* 64:55–64 (1991).

McManus et al., "Direct myocardial injury by enterovirus: a central role in the evolution of murine myocarditus," *Clin. Immunol. Immunopathol* 68:159–169 (1993).

Melnick et al., "Pathogenesis of coxsackie virus infection, Multiplication of virus and evolution of the muscle lesion in mice," *J. Expert. Med.* 93:247–266 (1951).

Anderson et al., "Direct interactins of coxsackievirus B3 with immune cells in the splenic compartment of mice susceptible or resistant to myocarditis," *J. Virol* 70:4632–4645 (1996).

Hohenadl et al., "Strand–specific detection of enteroviral RNA in myocardial tissue by in situ hybridization," *Mol. Cell. Probes* 5:11–20 (1991).

Pfeffer et al., "Influence of Chronic Captopril Therapy on the Infacted Left Ventricle of the Rat," *Circ. Res.* 57:84–95 (1985).

Bishop et al., "Three abundance classes in HeLa cell messenger RNA," *Nature* 250(463):199–204 (1974).

Hedrick et al., "Isolation of cDNA clones encoding T–cell –specific membrane–associated proteins," *Nature* 308: (1984).

Nolet et al., "Rapid Evolution of prostatic protein $PSP_{94}$ suggested by sequence divergence between Rhesus monkey and human cDNAs," *Genomics* 9:775–777 (1991).

Valtier et al., "Binding sites for a peripheral type benzodiazepine antagonist ([$^3$H] PK 11195) in human iris," *Neuropharmacology* 26:549–552 (1987).

J05122: Rat peripheral-type benzodiazepine receptor (RPBS)
       mRNA (SEQ ID NO: 1)

M36035: Human peripheral benzodiazepine receptor (hpbs)
       (SEQ ID NO: 2)

Percent Similarity: 74.613  Percent Identity: 74.485

J05122.seq x M36035.seq

```
  5  GATCTTTCCAGAACAGCAGTTGCAATCACTATGTCTCAATCCTGGGTACC   54
     || ||  ||  |||||||| ||||    |  ||| |  |   |||||| ||
 32  GAGCTCCCCTGAACAGCAGCTGCAGCAGCCATGGCCCCGCCCTGGGTGCC   81

55  CGCCGTGGGCCTCACTCTGGTGCCCAGCCTGGGGGGCTTCATGGGAGCCT  104
     ||||  |||||  ||| ||||  ||||||||||| |||||  |||||| ||
 82  CGCCATGGGCTTCACGCTGGCGCCCAGCCTGGGGTGCTTCGTGGGCTCCC  131

105  ACTTTGTGCGTGGTGAGGGCCTCCGCTGGTATGCTAGCTTGCAGAAACCC  154
     ||||||  |   ||  ||||| |||||||||||  ||  |||||||| |||
132  GCTTTGTCCACGGCGAGGGTCTCCGCTGGTACGCCGGCCTGCAGAAGCCC  181

155  TCCTGGCATCCGCCTCGCTGGACACTCGCTCCCATCTGGGGCACACTGTA  204
     || ||||||  ||||| |  ||||   ||  |||||||||||||| || ||
182  TCGTGGCACCCGCCCCACTGGGTGCTGGGCCCTGTCTGGGGCACGCTCTA  231

205  TTCGGCCATGGGGTATGGCTCCTACATAATCTGGAAAGAGCTGGGAGGTT  254
     ||  |||||||||||| |||||||| |||||| |  |||||||||||||||  |
232  CTCAGCCATGGGGTACGGCTCCTACCTGGTCTGGAAAGAGCTGGGAGGCT  281

255  TCACAGAGGAGGCTATGGTTCCCTTGGGTCTCTACACTGGTCAGCTGGCT  304
     ||||||||   |||  ||||||| | |||| |||||||||||| |||||||
282  TCACAGAGAAGGCTGTGGTTCCCCTGGGCCTCTACACTGGGCAGCTGGCC  331

305  CTGAACTGGGCATGGCCCCCCATCTTCTTTGGTGCCCGGCAGATGGGVTG  354
     |||||||||||||||||||||||||||||||||||||||| || ||||| ||
332  CTGAACTGGGCATGGCCCCCCATCTTCTTTGGTGCCCGACAAATGGGCTG  381

355  GGCTTTGGTGGACCTCATGCTTGTCAGTGGGGTGGCAACCGCCACTACCC  404
     |||  |||||||| |  |||| ||||||||||||| || ||  |||||||||
382  GGCCTTGGTGGATCTCCTGCTGGTCAGTGGGGCGGCGGCNGCCACTACCG  431

405  TGGCTTGGCACCGAGTGAGCCCACCGGCTGCCCGCTTGCTGTATCCTTAC  454
     |||| ||| |||  |||||||||||||||| |  |||||||  || || |||
432  TGGCCTGGTACCAGGTGAGCCCGCTGGCCGCCCGCCTGCTCTACCCCTAC  481

455  CTGGCCTGGCTGGCCTTTGCCACCATGCTCAACTACTATGTATGGCGTGA  504
     |||||||||||||||||| || |||| |||||||||||| ||||||| ||
482  CTGGCCTGGCTGGCCTTCGCGACCACACTCAACTACTGCGTATGGCGGGA  431

505  TAACTCTGGTCGGCGAGGGGGCTCCCGGCTCACAGAGTGAGGACACCTAG  554
```

SEQ ID NO:3
M36035  Human peripheral benzodiazepine receptor
        CDS 62...57 1

```
agtgcccttc ccggagcgtg ccctcgccgc tgagctcccc tgaacagcag ctgcagcagc  60
catggccccg ccctgggtgc ccgccatggg cttcacgctg gcgcccagcc tggggtgctt 120
cgtgggctcc cgctttgtcc acggcgaggg tctccfctgg tacgccggcc tgcagaagcc 180
ctcgtggcac ccgccccact gggtgctggg ccctgtctgg ggcacgctct actcagccat 240
ggggtacggc tcctacctgg tctggaaaga gctgggaggc ttcacagaga aggctgtggt 300
tcccctgggc ctctacactg ggcagctggc cctgaactgg gcatggcccc ccatcttctt 360
tggtgcccga caaatgggct gggccttggt ggatctcctg ctggtcagtg gggcggcggc 420
ngccactacc gtggcctggt accaggtgag cccgctggcc gcccgcctgc tctaccccta 480
cctggcctgg ctggccttcg cgaccacact caactactgc gtatgccggg acaaccatgg 540
ctggcatggg ggacggcggc tgcagagtg agtgcccggc ttgtgatgtg gtggccgtca cgctttcatg ccaccaggga ctgcagctgc 600
accagcaggt gccatcacgc ttgtgatgtg gtggccgtca cgctttcatg accactgggc 660
ctgctagtct gtcagggcct tggcccaggg gtcagcagag cttcagaggt tgccccacct 720
gagccccac ccgggagcag tgtcctgtgc tttctgcatg cttagagcat gttcttggaa 780
catggaattt tataagctga ataagtttt tgacttcctt t  821
```

Sequence 1 (Query)
M181477
Human diazepam binding inhibitor (DBI) mRNA, complete cds.
Length 556
from: 1 to = 556

Sequence 2 (Subject)
M203924
Rat diazepam binding inhibitor (DBI) mRNA, complete cds.
Length 456
from: 1 to = 456

NOTE: The statistics (bitscore and expect value) is calculated
      bassed on the size of nr database Score = 235 bits (122), Expect = 5e-60
Identities = 222/272 (81%), Positives = 222/272 (81%)

Query:  78 aggctgagtttgagaaagctgcagaggaggttaggcaccttaagaccaagccatcggatg 137
            |||||||  ||||| ||||| ||||||||||||| | || ||| ||||| ||||| | ||||
Sbjct:  14 aggctgattttgacaaagccgctgaggaggtgaagcgcctcaagactcagccaactgatg 73

Query: 138 aggagatgctgttcatctatggccactacaaacaagcaactgtgggcgacataaatacag 197
            | ||||||||||||||||||  ||||| |||||||||| |||||||||||||  |||| ||||
Sbjct:  74 aagagatgctgttcatctacagccacttcaaacaagctactgtgggcgatgtaaacacag 133

Query: 198 aacggcccgggatgttggacttcacgggcaaggccaagtgggatgcctggaatgagctga 257
            |  |||||| ||| |||||||||| ||| ||||||| |||||||||||||  | ||||| ||||||
Sbjct: 134 atcggccggggctgttggacctcaagggcaaagccaagtgggactcgtggaacaagctga 193

Query: 258 aagggacttccaaggaagatgccatgaaagcttacatcaacaaagtagaagagctaaaga 317
            ||||  |||||||||||||||| ||||||||||||| | || |  |  | || |||||||||||||||
Sbjct: 194 aaggaacttccaaggaaaatgccatgaagacctatgtggaaaaggtagaagagctaaaga 253

Query: 318 aaaaatacgggatatgagagactggatttggt 349
            | ||||||  || ||||| || ||| |||||||||
Sbjct: 254 agaaatatggaatataaacgaccagatttggt 285

FIG. 3

Human Diazepam Binding Inhibitor

MWGDLWLLPPASANPGTGTEAEFEKAAEEVRHLKTKPSDEEMLFIYGHYKQATVGDINTERPGM
LDFTGKAKWDAWNELKGTSKEDAMKAYINKVEELKKKYGI

*FIG. 4*

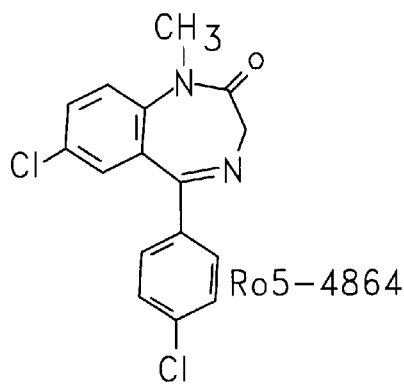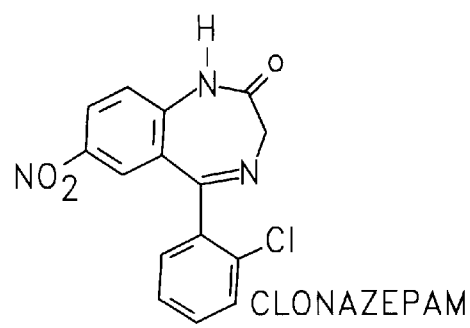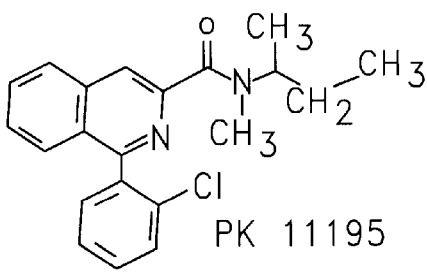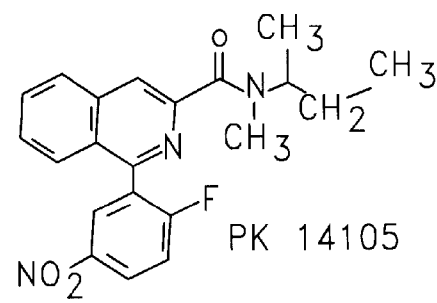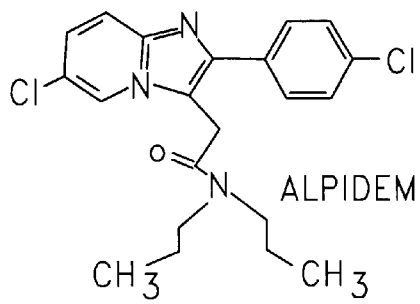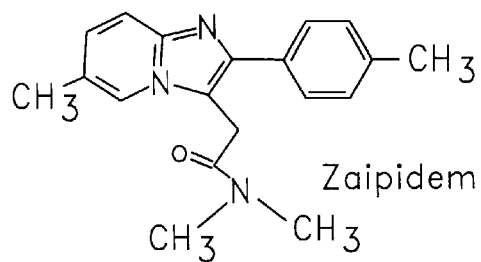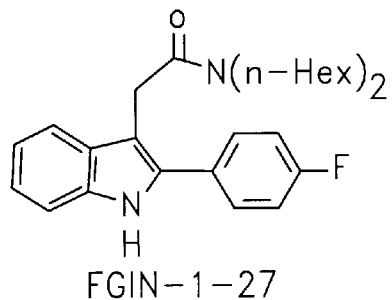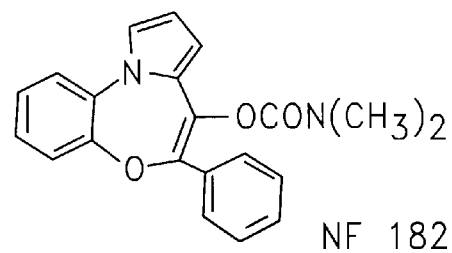
FIG. 5

TREATMENT OF DISEASES INVOLVING CYST FORMATION

A claim for the benefit of priority under 35 U.S.C. 119(e) of U.S. provisional application Ser. No. 60/113,008, filed Dec. 18, 1998, now abandoned which claim benefit to Provisional No. 60/136,208 filed May 26, 1999.

FIELD OF THE INVENTION

The present invention concerns the treatment of diseases involving cyst formation, such as polycystic kidney disease. The present invention also concerns various endogenous and exogenous ligands of peripheral-type benzodiazepine receptors, and in particular, their use in the prevention or treatment of cyst formation.

BACKGROUND OF THE INVENTION

A. Diseases Involving Cyst Formation

There are several human diseases that result in the formation of cysts containing either semi-solid or fluid material. Benign cysts can occur, for example, in the ovary, spleen, lungs, kidney and liver, where they are often hereditary., Cysts can be acquired, as in diverticulosis of the intestines, or acquired as a secondary cause of an-inherited disease, as in cystic fibrosis, or can be directly inherited, as in polycystic disease of the kidney, which can also affect the liver and brain.

Renal cysts arise in the renal parenchyma, and begin as dilations or outpouchings from existing nephrons or collecting ducts or from the developmental counterparts of these structures. Renal cysts contain a fluid that presumably derives from their parent nephtron and/or is a local secretion. They may be hereditary, developmental, or acquired, and may occur in the cortex, medulla or both, and may or may not be associated with other renal or systemic abnormalities. For further details see, for example, Brenner & Rector, *The Kidney*, Fourth Edition, 1991, Vol. II, pp. 1657–1659.

Polycystic kidney disease (PKD) is a subset of renal cystic disorders in which cysts are distributed throughout the cortex and medulla of both kidneys. PKD is usually the hallmark of a unique autosomal dominant (autosomal dominant polycystic kidney disease, ADPKD) or autosomal recessive (autosomal recessive polycystic kidney disease, ARPKD) disorder but may also be found in association with a variety of clinical conditions or acquired at some point of life by a patient with an underlying, noncystic renal disease. PKD is the most prevalent hereditary renal disorder, accounting for over 5 percent of patients on chronic hemodialysis.

ADPKD, the most common dominantly inherited kidney disease usually appears in midlife, and is characterized morphologically be massive cyst enlargement, moderate interstitial infiltration with mononuclear cells, and extensive fibrosis. Characteristic symptoms include proteinuria, abdominal pain and palpable kidneys, followed by hematuria, hypertension, pyuria, uremia and calculi. In about 15% of patients, death is due to cerebral aneurysm. ADPKD is caused by mutations in one of three genes: PKD1 on chromosome 16 accounts for approximately 85% of cases whereas PKD2 on chromosome 4 accounts for approximately 15%. Mutations in the so far unmapped PKD3 gene are rare. (Reeders et al., *Nature* 317:542–544 [1985]; Kimberling et al., *Genomics* 18:467–472 [1993]; Daoust et al., *Genomics* 25:733–736 [1995]; Koptides et al., *Hum. Mol. Genet.* 8:509–513 [1999]).

ARPKD is a rare inherited disorder which usually becomes clinically manifest in early childhood, although presentation of ARPKD at later ages an survival into adulthood have also been observed in many cases. ARPKD was first studied in C57BL/6J mice in whom it arises spontaneously (Preminger et al., *J. Urol.* 127:556–560 [1982]). The cpk mutation characteristic of this disease has been mapped to mouse chromosome 12 (Davisson et al., *Genomics* 9:778–781 [1991]). The gene responsible for ARPKD in humans has been mapped to chromosome 6 p. More recently, fine mapping of the autosomal recessive polycystic kidney disease locus (PKHD1) has been reported (Mucher et al., *Genomics* 48:40–45 [1998]).

It has been reported that taxol and taxol derivatives inhibit the progression of PKD and prolongs the survival of polycystic cpk mice (Woo et al., *Nature* 368:750–753 [1994]; PCT publication WO 94/08041; U.S. Pat. No. 5,882,881). Since taxol specifically induces the expression of TNF-α in macrophages and lymphocytes, it has also been suggested that TNF-α is useful in the treatment of PKD (U.S. Pat. No. 5,750,495).

In APKD, the renal cysts remain small for 30–40 years. They then start to expand, progressively replacing normally functioning renal parenchyma. Factors involved in cyst expansion include loss of epithelial differentiation, increased proliferation and apoptosis, secretion of chloride and other ions into the cyst fluid and the development of inflammation around the outer circumference of the cyst wall (Grantham, J. *Am J.Kid.Dis.* 28:788–803 [1996]).

There is a need for the identification of endogenous and exogenous factors that are suitable for the prevention and treatment of diseases involving cyst formation and cyst expansion. In view of the severity and frequency of occurrence of PKD, there is a particular need for finding therapeutic agents useful in the prevention and treatment of this disease.

B. Ligands of Peripheral-Type Benzodiazepine Receptors (PTBR)

Ligands of PTBR's have been known for many years and anti-anxiety CNS effects of PTBR agonists (e.g. Valium) are widely known. With respect to benzodiazepine receptors outside the CNS (PTBR) most of what is known concerns the role of such receptors in mediating muscle relaxation, particularly smooth muscle relaxation. Vagal tone has been found to decrease following intravenous administration of diazepamn. (Adinoff et al., Psychiatry Research 41:89–97 [1992]). There is evidence for control of cardiac vagal tone by benzodiazepine receptors (DiMicco, Neuropharmnacology 26:553–559 [1987]). PTBR ligands Ro5-4864 and PK 11195, but not diazepam, have been described to depress cardiac function in an isolated working rat heart model (Edoute et al., Pharmacology 46:224–230 [1993]). Ro5-4864 has also been reported to increase coronary flow in an isolated perfused Langendorf rat heart without affecting heart rate and left ventricular contractility. PK 11195 did not antagonize this vasodilatory effect (Grupp et al., Eur. J. Pharm. 143:143–147 [1987]). In an isolated rat heart preparation, diazepain induced a transient negative inotropic effect followed by a positive inotropic response. The positive inotropy was antagonized by PK 11195. (Leeuwin et al., Eur. J. Pharm. 299:149–152 [1996]). Diazepam increased contractile force in Langendorf rat heart., (Leeuwin et al., Arch. Int. Pharmacodyn. 326:5–12 [1993]). Ro5-4864 has been shown to have a small (20%) depressant effect on the contraction amplitude (negative inotropic effect) of human atrial strips that was not antagonized by PK 11195 (Shany et al., Eur.J. Pharm. 253:231–236 [1994]). In a guinea pig heart preparation Ro5-4864 decreased the duration of intracellular action potential and contractility. Diazepam was less effective and clonazepam ineffective. The effects of Ro5-4864 were reversed by PK 11195 but not by a specific antagonist of the CNS BZR. (Mestre et al., Life Sciences 35:953–962 [1984]). The presence of PTBR binding sites in the hearts of dogs and humans was demonstrated in vivo by positron emission tomography using [$^{11}$C]-PK 11195. (Charmonneau et al., Circulation 73:476–483 [1986]). It has also been reported that Ro5-4862 and dipyridamole can compete [$^3$H] diazepam binding to heart tissue. Diazepam potentiates the actions of adenosine on isolated cardiac and smooth muscle and the coronary vasodilator action of adenosine in dogs. There is evidence that diazepam may be acting in a similar manner to dipyridamole by inhibiting adenosine uptake. (Davies and Huston, Eur. J. Pharm. 73:209–211 [1981]).

More recently, PTBR's have been shown to play a role in cell pathways underlying apoptosis. PTBR's expressed on mitochondria serve as docking receptors for Bcl$_2$, a protein that inhibits apoptosis. The biological pathways in apoptosis modulated by PTBR ligand interactions are not specifically known.

SUMMARY OF THE INVENTION

The present invention is based on the recognition that ligands that interact with the PTBR's are useful in the treatment of diseases associated with cyst formation, and in particular, slow down or prevent the progression of polycystic kidney disease (PKD) to renal failure, and/or slow down or prevent the accompanying tendency toward hypertension.

In one aspect, the invention concerns a method for the treatment of a disease, involving cyst formation, comprising administering to a patient having or at risk of developing such disease an effective amount of a ligand of a peripheral-type benzodiazepine receptor (PTBR). The patient is preferably mammal, more preferably human. In a particular embodiment, the disease to be treated is polycystic kidney disease (PKD). In a preferred embodiment, the administration of a PTBR ligand prevents or slows down the progression of PKD. In another preferred embodiment, the administration of a PTBR ligand prevents or slows down the development of a symptom of PKD, such as, hypertension associated with PKD, bleeding into the cyst, or pain associated with cyst expansion.

In a further aspect, the invention concerns a method for the treatment of progressive renal insufficiency associated with the progression of cystic disease.

In another aspect, the invention concerns a method for the treatment of hypertension accompanying polycystic kidney disease (PKD) comprising administering to a patient an effective amount of a ligand of a peripheral-type benzodiazepine receptor (PTBR).

In yet another aspect, the invention concerns a pharmaceutical composition for the treatment of a disease involving cyst formation or cyst expansion, comprising an effective amount of a ligand of a peripheral-type benzodiazepine:receptor (PTBR) in admixture with a pharmaceutically acceptable carrier.

In a further aspect, the invention concerns article of manufacture comprising a container, an effective amount of a ligand of a peripheral-type benzodiazepine receptor (PTBR) within the container, and a label or package insert with instructions for administering the ligand for the treatment of a disease involving cyst formation.

In all aspects, the disease to be treated preferably polycystic kidney disease (PKD), including both autosomal dominant polycystic kidney disease (ADPKD) and autosomal recessive polycystic kidney disease (ARPKD). Treatment specifically includes prevention, and slowing down the progression of the disease. If the objective is to prevent or slow down the progression of PKD, patients susceptible to the disease can be diagnosed by identifying mutations in the PKD1, PKD2 or PKD3 genes that are associated with PKD.

In all aspects, the PTBR agonist may, for example, be a native sequence PTBR ligand or a fragment or functional subunit thereof, an organic small molecule or peptide, a polypeptide variant of a native sequence ligand, an antibody, a glycopeptide, a glycolipid, a polysaccharide, an oligosaccharide, a nucleic acid, a peptidomimetic, a pharmacological agent or a metabolite thereof, a transcriptional or translational control sequence, and the like. Similarly, the PTBR antagonist may be a polypeptide, an organic small molecule or peptide, a polypeptide variant of a native sequence ligand, an antibody, a glycopeptide, a glycolipid, a polysaccharide, an oligosaccharide, a nucleic acid, a peptidomimetic, a pharmacological agent or a metabolite thereof, a transcriptional or translational control sequence, and the like. For example, PTBR antagonists include polypeptide variants of a native sequence PTBR ligand, variants of a native sequence PTBR that retain the ability to bind an endogenous ligand but are deficient in their ability to mediate biological activity, anti-PTBR or anti-PTBR ligand antibodies, and selective inhibitors of the in vivo production of an endogenous PTBR ligand. The organic small molecules are preferably selected from the chemical classes of benzodiazepines, isoquinoline carboxamides, imidazopyridines, 2-aryl-3-indoleacetamides, and pyrolobenzoxazepines. A particularly preferred agonist is Ro5-4864, while a particularly preferred antagonist is PK 11195.

The PTBR ligands can be administered in combination with an additional therapeutic agent, preferably with an agent known to be useful to treat the target disease or a related condition. For example, the PTBR ligands of the present invention can be administered in combination with one or more therapeutic agents that inhibit the delivery of membrane proteins to the membrane of a cell of the patient treated. Such agents include, for example, taxol, cytochalasin-B, cytochalasin-D, phalloidin and derivatives of any of the foregoing, and TNF-α. The PTBR ligands can also be administered in combination with generic inhibitors or renal insufficiency progression, such as anti-hypertension therapeutics, including ACE inhibitors.

Administration can be performed by various routes known in the art, including, without limitation, intravenous, intraperitoneal, intraarterial, subcutaneous, oral or intramuscular administration.

BRIEF DESCRIPTION OF THE FIGURES

FIG. 1 shows alignment data comparing the cDNA encoding the differentially expressed rat peripheral-type benzodiazepine receptor (P0268) gene with human cDNA corresponding to PTBR (SEQ ID NOs: 1 and 2).

FIG. 2 shows the amino acid sequence of human PTBR (SEQ ID NO:3).

FIG. 3 shows alignment data comparing the cDNA encoding the differentially expressed rat diazepam binding inhibitor (DBI) gene with human cDNA corresponding to DBI (SEQ ID NOs: 4 and 5).

FIG. 4 shows the amino acid sequence of human DBI (SEQ ID NO: 6).

FIG. 5 shows the chemical structure of selected PTBR ligands, including PTBR agonist Ro5-4864, and antagonist PK 11195.

DETAILED DESCRIPTION OF THE INVENTION

I. Definitions

Figure 6:
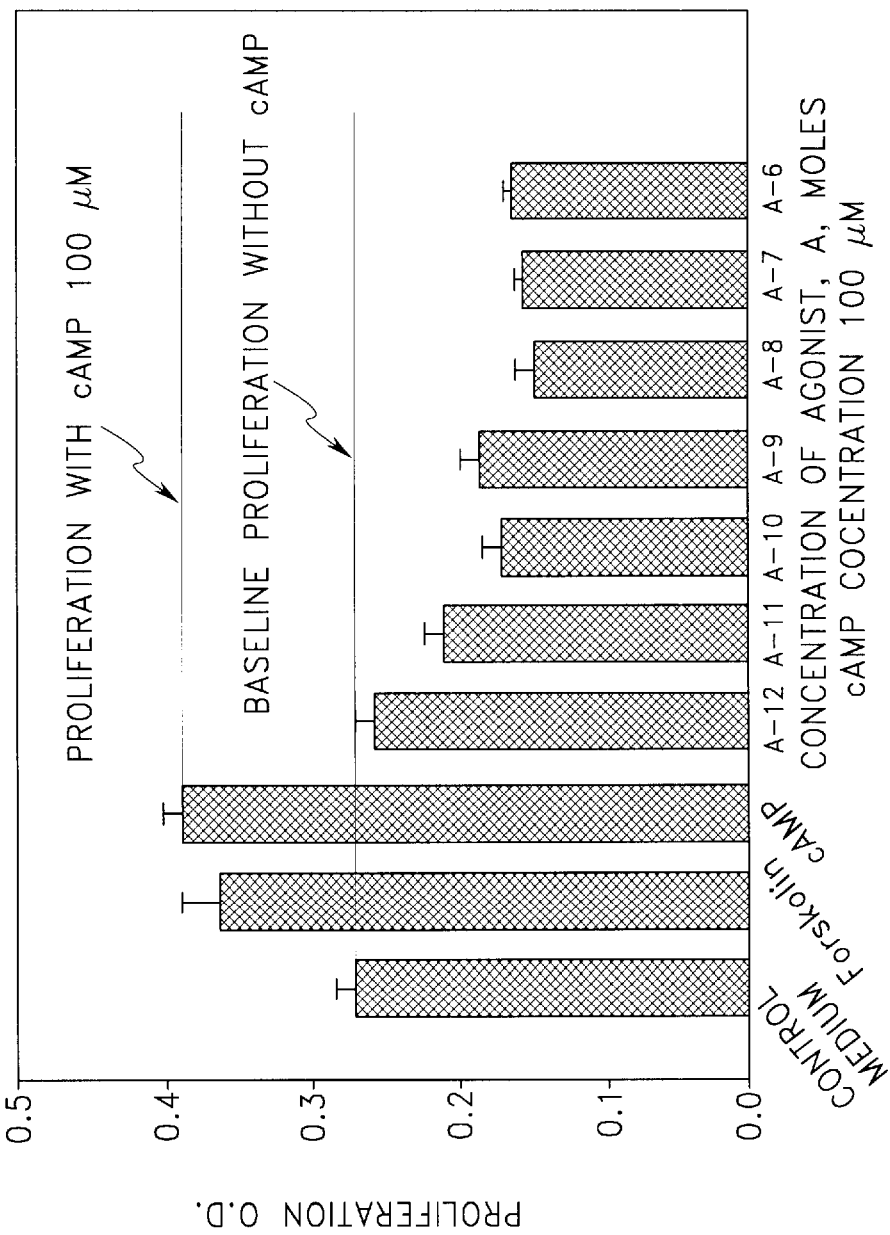
FIG. 6 is a graphical illustration of the effect of PTBR agonist, Ro5-4864 on the proliferation of human ADPKD cells. In the Figure, "A" represents Ro5-4864, and the numbers following represent the molar concentrations of the agonist. Thus, "–12" following "A" means that the agonist Ro5-4864 was used in a concentration of $10^{-12}$ M.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York,. NY 1994), and March, *Advanced Organic Chemistry Reactions, Mechanisms and Structure* 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The terms "peripheral-type benzodiazepine receptor", "PTBR", and "PTBR polypeptide", whether used in singular or plural, are used interchangeably, and encompass any native sequence PTBR polypeptide. Such PTBR polypeptides can be isolated from a variety of sources, such as from a variety of human or non-human tissue types, or prepared by recombinant and/or synthetic methods. All such polypeptides are specifically within the scope of the definition, regardless of their mode of preparation, and include variants thereof. Thus, the terms "peripheral-type benzodiazepine receptor", "PTBR", and "PTBR polypeptide", whether used in singular or plural, refer to receptor polypeptides which bind to benzodiazepine molecules but are distinct from those associates with the central-type benzodiazepine receptors, and which have the same amino acid sequence as a respective polypeptide derived from nature. Such PTBR polypeptides can be isolated from nature or can be produced by recombinant and/or synthetic means. The term "PTBR" specifically encompasses naturally-occurring truncated or secreted forms (e.g., an extracellular domain sequence), as well as naturally occurring variant forms (e.g., alternatively spliced forms), and naturally occurring allelic variants. PTBR's represent a subset of the benzodiazepine receptor family that is located outside the central nervous system. Kruger et al., in: *GABA and Benzodiazepine Receptor Subtypes*, Biggio and Costa eds., pp. 1–14 (1990) reported the purification, cloning and expression of a peripheral-type benizodiazepine receptor. The cDNA of a 18-kDa PTBR polypeptide, originally identified in heart tissue, has subsequently been cloned from various sources, such as rat adrenal (Sprengel et al., *J. Biol. Chem.* 264:20,415–20,421 [1989]); bovine adrenal (Parola et al.; *J. Biol. Chem.* 266:14, 082–14,087 [1991]); a human lymphoma cell line (Riond et al., *Eur. J. Biochem.* 195:305–311 [1991]); and a mouse Leydig tumor cell line (Gamier et al., *Mol. Pharmac.* 45:201–211 [1993]). This 169 amino acid protein has approximately 80% homology between species. Various cells transfected with these cDNAs displayed binding characteristics for PTBR ligands Ro5-4864 and PK 11195. It has been suggested that PTBR is a multimeric complex in which the PK 11195 binding site is on the 18-kDA subunit, and expression of the benzodiazepine binding requires another subunit, designated VDAC. Another, 10-kDa protein, associated with PTBR, has also been tentatively identified as a further component of the PTBR complex. (See, e.g. Zisterer and Williams, supra.) All of these polypeptides, alone, or in any functional combination, are specifically within the definition of"PTBR". In a particular embodiment, the peripheral-type benzodiazepine receptor has the amino acid sequence of human PTBR (SEQ ID NO: 3).

The terms "ligand" "PTBR ligand" and "ligand of a (native sequence) PTBR" are interchangeable, and are used in the broadest sense to include endogenous or exogenous factors that interact with a PTBR, including native sequence PTBR ligands and their variants, as well as synthetic polypeptide or small molecule ligands. The "interaction" is defined as the ability to affect the function of a PTBR may, but does not need to involve, specific binding to the native sequence PTBR. The term "PTBR-ligand" includes antagonists and agonists, as defined below.

The terms "native sequence ligand", "native sequence PTBR ligand", "native sequence ligand of a PTBR", and grammatical equivalents thereof, are used interchangeably, and refer to endogenous ligands of a PTBR, known or hereinafter discovered. Such native sequence polypeptides can be isolated from nature or can be produced by recombinant and/or synthetic means. The term "native sequence" in conjunction with the designation of a particular polypeptide specifically encompasses naturally-occurring truncated or secreted forms (e.g., an extracellular domain sequence), as well as naturally occurring variant forms (e.g., alternatively spliced forms), and naturally occurring allelic variants of the named polypeptide.

The term "antagonist" is used in the broadest sense and includes any molecule that partially or fully blocks, inhibits or neutralizes a biological activity mediated by a native sequence PTBR through preventing the binding of an agonist to the native sequence PTBR, thereby blocking the biological activity of the agonist mediated by the PTBR. In a similar manner, the term "agonist" is used in the broadest sense and includes any molecule that mimics a biological activity mediated by a PTBR, and specifically changes the function or expression of a PTBR, or the efficiency of signalling through a PTBR, thereby altering (increasing or inhibiting) an already existing biological activity or triggering a new biological activity.

The terms "variant" and "amino acid sequence variant" are used interchangeably and designate polypeptides in which one or more amino acids are added and/or substituted and/or deleted and/or inserted at the N- or C-terminus or anywhere within the corresponding native sequence, and which retain at least one activity (as defined below) of the corresponding native polypeptide. In various embodiments, a "variant" polypeptide usually has at least about 75% amino acid sequence identity, or at least about 80% amino acid sequence identity, preferably at least about 85% amino acid sequence identity, even more preferably at least about 90% amino acid sequence identity, and most preferably at least about 95% amino acid sequence identity with the amino acid sequence of the corresponding native sequence polypeptide.

"Sequence identity", is defined as the percentage of amino acid residues in a candidate sequence that are identical with the amino acid residues in a native polypeptide sequence, after aligning the sequences and introducing gaps, if necessary, to achieve the maximum percent sequence identity, and not considering any conservative substitutions as part of the sequence identity.

The local homology algorithm of Smith and Waterman (Smith et al., *Adv. Appi. Math.* 2:482 (198 1)) can conduct optimal alignment of sequences for comparison, e.g., by the homology alignment algorithm of Needleman and Wunsch (Needleman et al., *J. Mol. Biol.* 48:443 (1970)), by the search for similarity method of Pearson and Lipman (Pearson et al., *Proc. Natl. Acad. Sci. USA* 85:2444 (1988)), by computerized implementations of these algorithms (GAP, BESTFIT, FASTA, and TFASTA in the Wisconsin Genetics Software Package, Genetics Computer Group, 575 Science Dr., Madison, Wis.), or by inspection.

In a preferred embodiment, the homology alignment algorithms employed in the BLAST program (Altschul et al., *Nucleic Acids Res.* 25:3389–3402 (1997)) may be used. The BLAST family of programs allows all combinations of DNA or protein query sequences with searches against DNA or protein databases. Within the context of the present invention, the specific BLAST programs that may be utilized include: blastp, which compares an amino acid query sequence against a protein sequence database; blastn, which compares a nucleotide query sequence against a nucleotide sequence database; blastx, which compares the six-frame conceptual translation products of a nucleotide query sequences (both strands) against a protein sequence database; tblastn, which compares a protein query sequence against a nucleotide sequence database dynamically translated in all six reading frames (both strands); and tblastx, which compares the six-frame translations of a nucleotide query sequence against the six-frame translations of a nucleotide sequence database. For the blastn program, the following parameters and their default values are utilized: -G: cost to open a gap, default=5; -E: cost to extend a gap, default=2; -q: penalty for a mismatch in the blast portion of run, default=-3; -r: reward for a match in the blast portion of run, default=1; -e: expectation value (E), default=10.0; -W: word size, default is 11 for blastn, 3 for other programs; -v number of one-line descriptions (V), default=100; and -b: number of alignments to show (B), default=100.

Most preferably, the % sequence identity values are generated by the NCBI BLAST2.0 software as defined by Altschul et al., (1997), "Gapped BLAST and PSI-BLAST: a new generation of protein database search programs", *Nucleic Acids Res.*, 25:3389–3402. The parameters are set to default values, with the exception of the Penalty for mismatch, which is set to −1.

"Active" or "activity" means a qualitative biological and/or immunological property. In the context of the present invention, a preferred biological activity of a PTBR antagonist is the ability to prevent, slow down the progression of or eliminate cyst formation or cyst expansion, or treat a disease dependent upon or mediating cyst formation. Even more preferably, a PTBR antagonist is biologically active, if it is effective in the treatment of polycystic kidney disease (PKD).

The phrase "immunological property" means immunological cross-reactivity with at least one epitope of the reference (native sequence) polypeptide molecule, wherein, "immunological cross-reactivity" means that the candidate polypeptide is capable of competitively inhibiting the qualitative biological activity of the reference (native sequence) polypeptide. The immunological cross-reactivity is preferably "specific", which means that the binding affinity of the immunologically cross-reactive molecule identified to the corresponding polypeptide is significantly higher (preferably at least about 2-times, more preferably at least about 4-times, most preferably at least about 6-times higher) than the binding affinity of that molecule-to any other known native polypeptide.

The phrases "polycystic kidney disease" "PKD" and "polycystic renal disease" are used interchangeably, and refer to a group of disorders characterized by a large number of cysts distributed throughout dramatically enlarged kidneys. The resultant cyst development leads to impairment of kidney function and can eventually cause kidney failure. "PKD" specifically includes autosomal dominant polycystic kidney disease (ADPKD) and recessive autosomal recessive polycystic kidney disease (ARPKD), in all stages of development, regardless of the underlying cause.

The terms "treat" and "treatment" refer to both therapeutic treatment and prophylactic or preventative measures, wherein the object is to prevent or slow down (lessen) an undesired physiological change or disorder, or the expansion of such disorder, such as the development of polycystic kidney disease. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

"Clironic" administration refers to administration of the agent(s) in a continuous mode as opposed to an acute mode, so as to maintain the desired effect for an extended period of time.

"Intermittent" administration is treatment that is not consecutively done without interruption, but rather is cyclic in nature.

Administration "in combination with" one or more further therapeutic agents includes simultaneous (concurrent) and consecutive administration in any order.

An "individual" is a vertebrate, preferably a mammal, more preferably a human.

"Mammal" for purposes of treatment refers to any animal classified as a mammal, including humans, domestic and farm animals, and zoo, sports, or pet animals, such as dogs, horses, cats, cows, etc. Preferably, the mammal herein is human.

An "effective amount" is an amount sufficient to effect beneficial or desired clinical results. An effective amount can be administered in one or more administrations. For purposes of this invention, an effective amount of a PTBR ligand is an amount that is sufficient to effect the desired treatment, as hereinabove defined.

The term "recombinant" when used with reference to a cell, animal, or virus indicates that the cell, animal, or virus encodes a foreign DNA or RNA. For example, recombinant cells optionally express nucleic acids (e.g., RNA) not found within the native (non-recombinant) form of the cell.

The term "antibody" is used in the broadest sense and specifically covers antiPTBR monoclonal antibodies (including agonist, antagonist, and neutralizing antibodies), polyclonal antibodies, multi-specific antibodies (e.g., bispecific antibodies), as well as antibody fragments. The monoclonal antibodies. specifically includes "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816, 567; Morrison et al., *Proc. Natl. Acad. Sci. USA*, 81:6851–6855 (1984)). The monoclonal antibodies further include "humanized" antibodies or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature*, 321:522–525 (1986); and Reichmann et al., *Nature*, 332:323–329 (1988). The humanized antibody includes a PRIMATIZED® antibody wherein the antigen-binding region of the antibody is derived from an antibody produced by immunizing macaque monkeys with the antigen of interest.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10):1057–1062 (1995)); single-chain antibody molecules; and multispecific antibodies formed from antibody fragments.

II. Modes of Carrying Out the Invention
A. Ligands of PTBR

There are several native polypeptides that have been putatively identified as endogenous ligands for PTBR or as components of such ligands. One possible endogenous ligand is the diazepam-binding inhibitor (DBI) (Berkovich et al., *Mol. Pharmac.* 37:164–172 [1990]; Guidotti et al., *Nature* 257:533–535 [1978]), an endogenous 11-kDa polypeptide of 86 amino acids (Besman et al., *Proc. Natl. Acad. Sci. USA* 86:4897–4901 [1989]). The same ligand is also referred to in the literature as acyl coenzyme A-binding protein (Knudsen et al., *Biochem. J.* 26:513–519 [1989]). This ligand is not selective as it has the same affinity ($\mu$M range) for both the GABA$_A$/benzodiazepine receptor and PTBR. A shorter fragment of DBI (fragment 17–50, also referred to as trikontetraneuropeptide) is more selective for PTBR.

Another set of putative endogenous ligands are naturally occurring porphyrins which have been reported to have high affinity for the PTBR. (Taketani et al., *J. Biochem.* 117:875–880 [1995] and Zisterer and Williams, supra.)

Synthetic ligands of the PTBR are also known and well characterized. Such synthetic ligands include benzodiazepines, such as, for example, Ro5-4864 and Clonazepam; isoquinoline carboxamides, e.g. PK 11195 [1-(2-chlorophenyl)-N-methyl-N-(1-methylpropyl)-3-isoquinoline carboxamide] and PK 14105 [(2-fluoro-5-nitrophenyl)-N-methyl-N-(1-methylpropyl)-3-isoquinoline carboxamide]; imidazopuridines, e.g. Alpidem and Zolpidem; and 2-amyl-3-indoleacetamides, e.g. FGIN-1-27; and pyrolobenoxapines, e.g. NF 182. The chemical structures of some selected synthetic PTBR ligands are shown in FIG. 5. Further synthetic PTBR ligands are also well known in the art, and are discussed, for example, in Zister and Williams, supra; Anzini et al., *J. Med. Chem.* 4275 (1996); Cappelli et al., *J. Med. Chem.* 2910 (1997) (conformationally constrained analogues of Ro5-4864); WO 96/32383 [(2-phenyl-pyrimidin-4-yl) (oxy or amino) acetamide derivatives]; FR 2,678,269 [1-(4-chlorophenyl)-2-(1-piperidinyl)ethanol derivatives]; EP 524,846 [2-(1-piperidinyl)-2-(6-(3,4-quinolin-2-(1H)-one))-ethanol derivatives]; FR 2,669,926 (phenylurea derivatives); U.S. Pat. No. 5,128,338 and EP 446,141 [imidazo(1,2-c)quinazoline derivatives]; U.S. Pat. No. 5,026,711 (4-substituted amino-quinoline or naphtyridine-3-carboxylic acid derivatives); U.S. Pat. No. 4,808,599 and EP 248,734 (benzothiphene or benzofuran carboxamide derivatives); and EP 210,084 (amide or carbamate derivatives of (iso)quinoline and quinazoline), the disclosures of which are hereby expressly incorporated by reference.

The use of these and similar ligands, native or synthetic, known or hereinafter discovered, is specifically within the scope of the present invention. Preferred ligands show high selectivity for the PTBR, relative to the benzodizepine receptors present in the brain (CBR) or GABA. In competitive binding experiments, the difference in binding affinity is preferably at least 10-fold, more preferably at least 100-fold, most preferably at least 1000-fold.

PTBR ligands include agonist and antagonist of PTBR. Representative PTBR agonists include benzodiazepines, e.g. Ro5-4864 and its derivatives, while representatives PTBR antagonists include isoquinoline carboxamides, e.g. PK 11195 and PK 14105 and derivatives.

B. Screening for New Antagonists and Agonists of PTBR.

The first step in identifying new ligands of the PTBR (whether agonists or antagonists), is in vitro screening to identify compounds that selectively bind the peripheral-type receptor. Receptor-binding can be tested using peripheral-type and brain-derived receptors isolated from their respective native sources, or produced by recombinant DNA technology and/or chemical synthesis. The binding affinity of the candidate compounds can be tested by direct binding (see, e.g. Schoemaker et al., *J. Pharmacol. Exp. Ther.*, 285:61–69 [1983]) or by indirect, e.g. competitive, binding. In competitive binding experiments, the concentration of a compound necessary to displace 50% of another compound bound to the receptor ($IC_{50}$) is usually used as a measure of binding affinity. The other ligand can be any compound known to bind to PTBR with high affinity and selectivity, e.g. PK 11195 or Ro5-4864.

In a specific embodiment, in order to identify novel ligands, DNA encoding the full length sequence of the human peripheral benzodiazepine receptor (GenBAnk M36035) is cloned into an expression vector containing a selectable marker. The vector is used to transfect recombinant host cells, for example mammalian cells, e.g., the human embryonic kidney cell line (HEK-293). Following several rounds of selection stable lines which express PTBRs are identified by Western blot using immunoreactivity toward an epitope tag that is genetically engineered into the PTBR gene. Membrane fractions are prepared from the stably expressing cell lines in bulk and stored frozen for HTP screening. Authentification of the PTBR containing membrane fractions is achieved by reproducing binding coefficients of known radiolabelled ligands (such as [3H] Ro5-4864). Screening for novel ligands is performed by virtue of their ability to compete effectively with [3H]Ro5-4864 in competitive binding assays. Binding coefficients can be determined by any known manner, e.g. by Scatchard analysis.

It might also be necessary to distinguish between PTBR agonists and antagonists. This can be done in in vitro or in vivo experiments, by monitoring the response of a cell following the binding of the ligand to the receptor. An agonist will produce a cellular response, which results in increased or new activity or in the inhibiting of an already occurring cellular activity. In contrast, an antagonist will have no effect on cellular response, rather will have the effect of preventing binding of agonists to the same receptor sites. It may be desirable to screen for antagonists in a fashion that the readout is functional to find molecules that activate the receptor without affecting the binding site(s) of the native ligand(s). Antagonists can be screened in a similar fashion.

For example, the following methods are suitable for identifying antagonists and agonists of the PTBR that are useful in the methods of the present invention:

1. The proliferation of renal epithelial, fibroblast, or smooth muscle cells derived from normal or polycystic mammalian (including human) kidneys.
2. The regulation of induced apoptosis in renal epithelial or fibroblast cells derived from normal or polycystic mammalian (including human) kidneys.
3. Monitoring the in vitro formation of cysts by cells derived from human or non-human mammals with polycystic kidney disease.
4. The expression of a phenotype indicating loss of differentiation by renal epithelial cells.
5. Alterations in ion conductance or in electrical phenomena dependent on ion conductance in renal epithelial cells or insterstitial cells derived from normal or polycystic kidneys.
6. Modulation in the secretion by renal or circulating cells of protein or lipid or carbohydrate factors associated with the expression or progression of polycystic kidney disease, including cytokines and lipid factors produced in or around cysts.

C. Other PTBR Antagonists

The PTBR antagonists of the present invention are not limited to PTBR ligands.

Other PTBR antagonists include (1) variants of a native PTBR that retain the ability to bind an endogenous PTBR ligand but are deficient in their ability to mediate a biological response, (2) soluble receptors, (3) antibodies specifically binding an endogenous PTBR ligand at or around its receptor binding site so that they block the binding of the ligand to its native receptor, and (4) selective inhibitors of the in vivo production of an endogenous PTBR ligand, such as transcriptional regulators of the expression of an endogenous PTBR ligand in vivo. Another preferred PTBR antagonist is a bioorganic molecule, usually an orally active compound that is based on synthetic and/or molecular modeling studies, that is capable of preventing the interaction between a native PTBR receptor and its endogeneous ligand. Such PTBR antagonists can be identifying using the same type of assays as those discussed above.

D. Availability of PTBR Antagonists and Agonists

The PTBR antagonist and agonists of the present invention can be small molecules, e.g. organic compounds or peptides that can be synthesized by known techniques of chemical synthesis. Some PTBR antagonists or agonists will be polypeptides, e.g. native sequence PTBR ligands, or fragments, variants or derivatives thereof, and may be produced by recombinant DNA technology, chemical synthesis or a combination of these or similar techniques. Some PTBR agonist or antagonists are commercially available, e.g. from Hoffmann-La Roche AG (Nutley, N.J.), and Synthelabo (France).

The PTBR ligands, either agonists or antagonist, of the present invention may also be agonist or antagonist antibodies to a PTBR. Methods of preparing polyclonal antibodies are known in the art. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. It may be useful to conjugate the immunizing agent to a protein known to be immunogenic in the mammal being immunized, such as serum albumin, or soybean trypsin inhibitor. Examples of adjuvants which may be employed include Freund's complete adjuvant and MPL-TDM.

According to one approach, monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing-agent to elicit lymphocytes that produce or are capable of producing antibodies that will specifically bind to the immunizing agent. Alternatively, the lymphocytes may be immunized in vitro. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. Preferred immortalized cell lines are those that fuse efficiently, support stable high level expression of antibody by the selected antibody-producing cells, and are sensitive to a medium such as HAT medium.

The culture medium in which the hybridoma cells are cultured can then be assayed for the presence of monoclonal antibodies directed against the particular PTBR used. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and PPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Alternatively, monoclonal antibodies may be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells discussed above serve as a preferred source of such DNA. Once isolated, the DNA may be placed into expression vectors, which are then transfected into host cells such as COS cells, Chinese hamster ovary (CHO) cells, or myeloma cells that do not otherwise produce immunoglobulin protein, to obtain the synthesis of monoclonal antibodies in the recombinant host cells.

The antibodies, including antibody fragments, such as Fv, Fab, Fab', F(ab')$_2$ or other antigen-binding subsequences of antibodies, may be humanized. Humanized antibodies contain minimal sequence derived from a non-human immunoglobulin. More specifically, in humanized antibodies residues from a complementary determining region (CDR) of a human immunoglobulin (the recipient) are replaced by residues from a CDR of a non-human species (donor antibody) such as mouse, rat or rabbit having the desired specificity, affinity and capacity. In some instances, Fv framework residues of the human immunoglobulin are also replaced by corresponding non-human residues. Humanized antibodies may additionally comprise residues that are found neither in the recipient antibody nor in the imported CDR or framework sequences [Jones et al., *Nature*, 321:522–525 (1986); Riechnann et al., *Nature*, 332:323–329 (1988)].

Methods for humanizing non-human antibodies are well known in the art. Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. In addition, human antibodies can be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

The antibodies may be bispecific, in which one specificity is for a PTBR, and the other specificity for another protein, such as, a second, different PTBR, or a different epitope of the same PTBR, or a PTBR ligand.

D. Compositions Comprising PTBR Agonists and Antagonists

The PTBR agonists and-antagonists (ligands and others) can be administered to a patient at therapeutically effective doses to treat (including prevention) a specific cystic disease, e.g. polycystic kidney disease. A therapeutically effective dose refers to that amount of the compound sufficient to result in desired treatment.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds exhibiting large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon-the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound, which achieves a half-maximal inhibition of symptoms) as determined in cell culture. Such information can be used to accurately determine useful doses in humans. Levels in plasma can be measured, for example, by high performance liquid chromatography. A typical daily dose for a PTBR agonist or antagonist of the present invention might range from about 1 µg/kg to about 100 mg/kg of patient body weight or more per day, depending on the factors mentioned above, preferably about 10 µg/kg/day to 10 mg/kg/day.

Pharmaceutical compositions for use in accordance with the present invention can be formulated in conventional manner using one or more physiologically acceptable car1 riers or excipients. Thus, the compounds and their physiologically acceptable salts and solvates can be formulated for administration by inhalation or insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate. talc or silica); disintegrants (e.g., potato starch or sodium starch glycolate); or wetting agents (e.g., sodium lauryl sulfate). The.tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound. For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges:of e.g., gelatin for use in an inhaler or-insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing or dispersing agents. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

If an agonist or an antagonist is coadministered with another agonist or antagonist, or with another agent having similar biological activity, the different active ingredients may be formulated together in an appropriate carrier vehicle to form a pharmaceutical composition. The PTBR agonists of the present invention may, for example, be combined or otherwise coadministered with other therapeutics used in the treatment of the target disease, for example, polycystic kidney disease, including taxol and taxol derivatives, TNF-α, anti-hypertensives, including ACE inhibitors, therapeutics targeting protein factors or their receptors, etc.

E. Gene Therapy

The cystic diseases, e.g. polycystic kidney disease, can be treated in accordance with the present invention also by gene-based therapies, using either ex vivo or in vivo transfer of a gene encoding a PTBR ligand polypeptide or other polypeptide PTBR agonist or antagonist. In the ex vivo form of gene delivery, cells derived either from the patient or from other sources, are first modified outside the body by introduction of a particular gene or genes. These modified cells are then reintroduced into the patient's body, so as to achieve local, regional or widespread distribution.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11:205–210 (1993)). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262:4429–4432 (1987); and Wagner et al., *Proc. Natl. Acad. Sci. USA* 87:3410–3414 (1990). For review 6 f the currently known gene marking and gene therapy protocols see Anderson et al., *Science* 256:808–813 (1992).

The most advanced technologies for using nucleic acids in the course of gene therapy use retroviral systems for delivering genes into the cell (Wilson et al., *Proc.Natl.Acad.Sci. U.S.A.* 87, 439–443 (1990), and Kasid et al., *Proc.Natl.Acad.Sci. U.S.A.* 87, 473–477 (1990).

Efficient gene transfer into the kidney is relatively difficult, particularly since the kidney is a structurally complex organ that has a relatively low mitotic index. Moreover, the architectural organization of the kidney is critical for proper organ function. Therefore, efficient gene delivery to one particular cell type within the kidney is relatively difficult to achieve. A specific method for gene transfer into the kidney is disclosed, for example, in U.S. Pat. No. 5,869,230 issued on Feb. 9, 1999. According to this approach, a vector carrying the genetic material of interest is introduced into the vasculature of the kidney under conditions that allow infection of kidney but protects it from ischemic damage, for example, by maintaining the kidney at a low temperature (e.g. on ice) during incubation with the gene transfer vector.

The following examples illustrate, but do not limit, the invention. All references cited throughout the specification, including the examples, are hereby expressly incorporated by reference.

EXAMPLE 1

Differential Expression of PTBR in an in vivo Model of Kidney Disease as Determined by Microarray Analysis The expression profile of representative genes was assessed in normal tissues and tissues obtained from subjects suffering from a disease, specifically cardiac, kidney or inflammatory disease. Identification of the differentially expressed genes involved the following steps: (1) construction of normalized and subtracted cDNA libraries from mRNA extracted from the cells or tissue of healthy animals and an animal model of disease; (2) purification of DNA; (3) microarraying the purified DNA for expression analysis; and (4) probing microarrays to identify the genes from the clones that are differentially expressed using labeled cDNA from healthy and diseased cells or tissues.

(1) In vivo Model of Kidney Disease

As an in vivo model of kidney disease, a rat model of an inherited form of autosomal dominant polycystic kidney disease (ADPKD) was used, based on the observation that ADPKD develops in Han:SPRD rats (Kaspareit-Rittinghaus et al., *Transplant Proc.* 6: 2582–3 (1990); Cowley et al., *Kidney Int.* 43:522–34 (1993)). Renal cysts and renal failure were evident in six months old male heterozygous rats (Cy/+), whereas control rats (+/+) showed no sign of cysts or renal failure. Five diseased animals (Cy/+) and one normal (+/+) were sacrificed and the kidneys removed.

(2) Preparation of Normalized and Subtracted cDNA Libraries

Poly A+mRNA was isolated from the kidneys of normal and diseased animals, following techniques known in the art, such as those described in Ausubel et al., eds., *Current Protocols in Molecular Biology*, J. Wiley and Sons (New York, N.Y. 1993). Large numbers of tissue samples can be readily processed using techniques well known in the art, such as, for example, the single-step RNA isolation process of Chomczynski (U.S. Pat. No. 4,843,155) which is hereby expressly incorporated by reference in its entirety. Methods for making normalized cDNA libraries are also well known in the art, see, e.g. Soares et al., *Proc. Natl. Acad. Sci. USA* 91(20):9228–32 (1994); and Bonaldo et al., *Genome Res.* 6(9):791–806 (1996). Following the method of Bonaldo et al., supra, a normalized version of a cDNA library was generated from normal and diseased tissue. In particular, poly A+RNA was purified from the normal and diseased tissue samples provided by the in vivo model of kidney disease described above. A directionally cloned cDNA library was first generated by conventional methods. Briefly, double stranded cDNA was generated by priming first strand synthesis for reverse transcription using oligo dT primers which contain a Not I restriction site. After second strand synthesis, Xba I adapters are added to the 5' end of the cDNA, and the cDNA size was selected for >500 bp and ligated into the corresponding restriction sites of phagemid vector pCR2.1 (Invitrogen, San Diego Calif.).

From the total CDNA library, a normalized library was generated as detailed elsewhere (Bonaldo et al., supra), and described here briefly. Phagemid vector pCR2.1 contains an F1 origin of replication. Thus, the cDNA library can be propagated as single stranded phage with appropriate helper virus. Single stranded, circular DNA was extracted from the phage library and serves as "tester" DNA in the hybridization step of normalization. The other component of the hybridization, "driver" DNA, was generated from the library by PCR amplification using a set of primers specific for the region of the vector, which flanks the cloned inserts. Purified tester DNA (50 ng) and driver DNA (0.5 $\mu$g) was combined in 120 mM NaCl, 50% formamide, 10 mM Tris (pH 8.0), 5 mM EDTA, and 1% SDS. A pair of oligonucleotides (10 $\mu$g each), corresponding to polylinker sequence (same strand as tester DNA) which is present in the PCR product, was included in the hybridization reaction to block annealing of vector-specific sequences which are in common between tester and driver DNA.

The reaction mixture, under oil, was heated 3 min. at 80° C., and hybridization performed at 30° C. for 24 hr (calculated $C_ot$~5). Single stranded circles were purified from the reaction mixture by hydroxylapatite (HAP) chromatography, converted to double strand DNA, and electroporated into bacteria to yield a normalized cDNA library representative of genes expressed in the left ventricle of rat. To evaluate the effectiveness of the normalization protocol, the frequency of a few clones (ANP, BNP, actin, and myosin) was assessed in both in the starting library and the normalized library. The frequency of abundant cDNAs (actin and myosin) was reduced and roughly equivalent to rarer cDNA clones (ANP and BNP). Clone frequency in the two libraries was determined with standard screening techniques by immobilizing colonies onto nylon membranes and hybridizing with radiolabeled DNA probes.

Certain genes, unexpressed in a normal tissue and turned on in diseased tissue, may be absent from the normalized cDNA library generated from normal tissue. To obtain disease-specific clones to include on the microarray, one can repeat the normalization strategy outlined above using diseased tissue obtained from the appropriate disease model. However, since most genes are expressed commonly between normal and diseased tissue, microarraying normalized libraries from diseased and normal tissue may introduce significant redundancy. In a preferred embodiment, clone redundancy is reduced, yet cDNAs are obtained which are expressed specifically, as well as substantially elevated, in diseased tissue. To obtain disease-specific cDNAs, a subtracted library can be made using protocols similar to those used to generate normalized libraries. Again, the method of Bonaldo et al., supra, described here briefly is used.

To make a subtracted library, a total cDNA library is generated from the tissue obtained from the disease model. The cDNA library is directionally cloned in pCR2.1 vector and single stranded tester DNA derived as described above for library normalization. The driver DNA is generated by PCR amplification of cloned inserts from the total CDNA: library prepared from the normal kidney. Hybridization occurs between sequences, which are in common to normal and diseased kidneys. For this subtracted library, the reaction is driven more thoroughly (calculated $C_{ot}$~27) than normalization by using more driver (1.5 µg vs. 0.5 µg) and longer hybridization time (48 hr vs. 24 hr). Purification of nonhybridized, single stranded circles by HAP chromatography, conversion to double strand DNA, and electroporation into bacteria yields a subtracted cDNA library enriched for genes which are expressed in diseased rat kidneys.

(3) Microarray Analysis

A microtiter plate protocol for PCR amplification of DNA and its subsequent purification was established that provides acceptable quality and quantity of DNA for printing on microarrays for use in a preferred embodiment of the present invention. Specifically, PCR primers were synthesized that amplify insert DNA from the vector pCR2.1, which was used for library construction. After 30 cycles of amplification each PCR product is passed over a gel filtration column to remove unincorporated primers and salts. To maintain robustness, the columns are packed in 96-well filter plates and liquid handling is performed robotically. The yield, per PCR reaction, is generally 2–5 µg, enough DNA for printing several hundred chips.

To test the quality of DNA that was prepared by this PCR method, 96 purified samples from a single microtiter plate were produced as a microarray. Using a robotic liquid handler (Biomek 2000, Beckman), 85 µl of PCR reaction mixture was aliquoted into each well of a thin walled, 0.2 ml 96-well plate. The reaction mixture contained 0.2 mM each dNTP, 1.25 units of Taq polymerase, and 1×Taq buffer (Boehringer Mannheim). Primers, 1 µm each, are from vector regions, which flank the cloning site of pCR2.1 and include a 5' primary amine with a 6 carbon linker to facilitate attachment of DNA product to the glass surface of the microarray chip. 1.0 µl of bacterial culture of individual cDNA clones was added to each well. PCR conditions are: 2 min., 95° C. to denature, then 30 cycles of 95°, 30 sec./65° C., 40 sec./72° C., 1 min. 30 sec., and a final extension of 72° C., 5 min. using a MJResearch PTC 100 thermocycler.

PCR products were purified by gel filtration over Sephacryl 400 (Sigma). Briefly, 400 µl of pre-swollen Sephacryl 400 was loaded into each well of a 96-well filter plate (PallBiosupport) and spun into a collection plate at 800 g for 1 min. Wells were washed 5 times with 0.2×SSC. PCR reaction mixtures were loaded onto the column and purified DNA (flow-thru) was collected at 800 g for 1 min. Samples are dried down at 50° C. overnight and arrayed.

Fluorescent probe pairs were synthesized by reverse transcription of poly A+RNA using, separately, Cy3 dCTP and Cy5 dCTP (Amersham). In 16.5 µl, 1 µg poly A+RNA and 2 µg of oligo dT 21mer, were denatured at 65° C., 5 min. and annealed at 25°C., 10 min. Reverse transcription was performed for 2 hours at 37° C. with Superscript RT (Life Technologies, Gaithersburg, Md.) in 1×buffer, 10 units RNase block, 500 µM each dATP/dGTP/dTTP, 280 µM dCTP, 40 µM Cy5 or Cy3 dCTP, and 200 units RT. RNA is degraded in 0.1 M NaOH, 65° C. for 10 min. Labeled cDNA was purified by successive filtration with Chroma Spin 30 spin columns (Clontech) following manufacturer's instructions. Samples were dried at room temperature in the dark using a covered Speed-Vac. Probes were applied to the test chip for hybridization and the data collected essentially as described in Schena et al., *Proc. Natl. Acad. Sci. USA* 93(20):106–49 (1996). The intensity of hybridization signal at each element reflected the level of expression of the mRNA for each gene in the rat ventricle. Digitized signal data was stored and prepared for analysis. A series of control DNA elements were included on each chip to ensure consistency in labeling and hybridization between experiments and to aid in balancing the signal when two fluorescence channels are used. For each element hybridized with dual labeled probes, absolute and relative intensity of signal was determined. The results from these and other experiments indicate that these methods for production of template DNA and labeled cDNA probes are suitable for generating high quality microarrays within a preferred embodiment of the methods of the present invention. The evaluation of tens of thousands of genes for expression generates a large amount of data that can be manipulated by commercially available software packages that facilitate handling this type and quantity of data. The expression data can be stored, analyzed, and sorted from each experiment using this software. In addition, expression of each clone can be tracked from experiment to experiment using known methodologies.

(4) Detection of Differentially Expressed Genes Using Microarray Analysis

As disclosed in detail above, probes were applied to the microarrays for hybridization and the data collected essentially as described in Schena et al., supra. The intensity of hybridization signal at each element reflected the level of expression of the mRNA for each gene. For each element hybridized with dual labeled probes, absolute and relative intensity of signal is determined, which translates into the relative expression levels of the subject genes. The numeric data generated reflects the relative expression level of the gene in the disease state as compared to the expression level of the gene in the normal, or non-disease state, in the five PKD disease model delineated above and as determined by microarray analysis. Data are reported as differential expression values with positive numbers indicative of genes expressed at higher levels in the diseased tissue relative to normal tissue, and negative values indicative of lower expression in disease. While in general microarray data are the average values from multiple experiments performed with separate DNA arrays, in the present case one experiment was performed and the RNA was obtained from one animal (n=1).

In a preferred embodiment, clones that reproducibly scored in microarray analysis to be at least about two-fold elevated or decreased were microarrayed on separate secondary chips and their expression levels determined. It is understood, however, that differentially expressed genes exhibiting less than about a two-fold change in expression, e.g., less than one, one-half, or one-quarter, or greater than about a two-fold change in expression, e.g., greater than three, five, ten, twenty, one hundred-fold, or one thousand-fold, are also of interest.

Using cDNA obtained from the in vivo kidney disease model, microarrays were constructed and probed as described above. It has been found that a gene, originally assigned clone ID No: P0242_B03 and later identified as the rat equivalent of human peripheral type benzodiazepine receptor (PTBR) gene, is overexpressed by a factor of 2 in the rat model of polycystic kidney disease (PKD) described above, as compared to normal kidney tissue. It has further been found that the gene for a native ligand of PTBR, DBI is underexpressed by a factor of –1.9 in diseased kidney tissue, as compared to normal tissue.

(5) Identification of Differentially Expressed Human Genes

Differentially expressed clones obtained from the microarray analysis of DNA obtained from the disease model described above were sequenced and compared to known human gene sequence databases for matches to known human genes. FIG. 1 shows alignment data comparing the nucleotide sequence of the cDNA encoding the differentially expressed rat P0268 gene with the sequence of human cDNA corresponding to PTBR (SEQ ID NOs: 1 and 2). FIG. 2 shows the amino acid sequence of human PTBR (SEQ ID NO: 3). FIG. 3 shows alignment data comparing the nucleotide of the cDNA encoding the differentially expressed rat DBI protein (native PTBR ligand) with the sequence of human cDNA corresponding to DBI (SEQ ID NOs: 4 and 5). FIG. 4 shows the amino acid sequence of human DBI.

EXAMPLE 2

Effect of a PTBR Agonist on Proliferation of Human ADPKD Cells

In this experiment, the effect of concentrations from $10^{-2}$ to $10^{-6}$ M of the known PTBR agonist, Ro5-4864 on the rate of proliferation of human autosomal dominant polycystic kidnay disease (ADPKD) cells was examined.

Epithelial cells from human ADPKD kidneys have been cultured from the domes of cysts and maintained in primary culture through several passages. These cells exhibit several phenotypic properties of intact cysts, including epithelial orientation, fluid secretion in response to cAMP stimulation and cell proliferation), and have been used for studies of cellular mechanisms of fluid secretion and cell proliferation.

The rate of cell proliferation was determined using the Promega Cell titer 96 MTT Assay method. This assay is a modification of that described by Mosmann T 1983 J Immunol Meth. 65, 55. This method, which measures the optical density (O.D.) of a proliferation-dependent reaction product (MTT), was found to correlate directly with direct determinations of cell number using the classical hemacytometer technique. The relation between cell number and O.D. was linear, and $r^2$ was >0.98. To determine the effect of agonists on the rate of proliferation, approximately 4000 cells were seeded into individual chambers of a 96-well plate. The cells were incubated initially in DME/F12 medium supplemented only with penicillin, streptomycin, ITS and 1% FBS. After 24 hours,.the FBS was reduced to 0.002% (ITS deleted) to arrest growth. This small amount of serum was needed to potentiate cell attachment to the plastic surface. The human ADPKD cells were then cultured for 48 hours, after adding the cAMP (a stimulator of cell proliferation) at a concentration of 100 μM. A control and forskolin group were examined as well. Preliminary studies determined that growth was sustained over this entire interval.

Thereafter the effect of a range of concentrations from $10^{-12}$ to $10^{-6}$ M of the known PTBR agonist, Ro5-4864 on the rate of proliferation of PTBR cells pretreated with cAMP or not treated (baseline proliferation) was examined. The results are graphically illustrated in FIG. 6. Each data set shown in FIG. 6 is mean, and was obtained from from six determinations. Accordingly, the results are highly statistically significant.

The data demonstrate that in all concentrations examined, Ro5-4864 acted as a potent inhibitor of cell proliferation, which blocked both basal cell proliferation and cAMP stimulated cell proliferation. Visual observation of the cells supports the finding that the PTBR agonist, Ro5-4864 acts by arresting cell growth and not be killing the cells.

What is claimed is:

1. A method for the treatment of a disease involving cyst formation comprising administering to a patient having or at risk of developing said disease an effective amount of a ligand of a peripheral-type benzodiazepine receptor (PTBR).
2. The method of claim 1 wherein said patient is a mammal.
3. The method of claim 2 wherein said patient is human.
4. The method of claim 3 wherein said disease is polycystic kidney disease (PKD).
5. The method of claim 4 wherein said PKD is autosomal dominant polycystic kidney disease (ADPKD).
6. The method of claim 4 wherein said PKD is autosomal recessive polycystic kidney disease (ARPKD).
7. The method of claim 4 wherein said treatment is prevention or inhibition of cyst expansion.
8. The method of claim 4 wherein said patient has been diagnosed with a mutation associated with polycystic kidney disease.
9. The method of claim 8 wherein said mutation is in the PKD1, PKD2, or PKD3 gene.
10. The method of claim 1 wherein said PTBR ligand is a native sequence PTBR ligand or a fragment or functional subunit thereof.
11. The method of claim 10 wherein said ligand is an endogenous ligand of a PTBR.
12. The method of claim 1 wherein said PTBR ligand is a synthetic ligand of a PTBR.
13. The method of claim 12 wherein said synthetic ligand is an organic compound.
14. The method of claim 13 wherein said organic compound is selected from the group consisting of benzodiazepines, isoquinoline carboxamides, imidazopyridines, 2-aryl-3-indoleacetamides, and pyrolobenzoxazepines.
15. The method of claim 1 wherein said ligand is a PTBR agonist.
16. The method of claim 4 wherein said ligand is a PTBR agonist.
17. The method of claim 15 wherein said PTBR agonist is Ro5-4864.
18. The method of claim 16 wherein said PTBR agonist is Ro5-4864.
19. The method of claim 4 wherein said ligand is administered in combination with an additional therapeutic agent.
20. The method of claim 19 wherein said additional therapeutic agent is an agent that inhibits the delivery of membrane proteins to the membrane of a cell of said patient.
21. The method of claim 20 wherein said additional therapeutic agent is selected from the group consisting of taxol, cytochalasin-B, cytochalasin-D, phalloidin and a derivative of any of the foregoing.
22. The method of claim 19 wherein said additional therapeutic agent is TNF-α.
23. The method of claim 4 wherein said ligand is administered an a pharmaceutical composition in admixture with a pharmaceutically acceptable carrier.
24. The method of claim 1 wherein said administration is intravenous, intraperitoneal, intraarterial, subcutaneous, oral or intramuscular.

* * * * *